(12) United States Patent
Bonnert et al.

(10) Patent No.: US 8,067,411 B2
(45) Date of Patent: Nov. 29, 2011

(54) COMPOUNDS

(75) Inventors: Roger Victor Bonnert, Loughborough (GB); Thomas McInally, Loughborough (GB); Tobias Mochel, Loughborough (GB); Stephen Thom, Loughborough (GB)

(73) Assignees: AstraZeneca AB, Sodertaje (SE); Dainippon Sumitomo Pharma Co., Ltd., Osaka (JP)

( * ) Notice: Subject to any disclaimer, the term of this patent is extended or adjusted under 35 U.S.C. 154(b) by 525 days.

(21) Appl. No.: 11/955,984

(22) Filed: Dec. 13, 2007

(65) Prior Publication Data

US 2008/0300244 A1 Dec. 4, 2008

Related U.S. Application Data

(60) Provisional application No. 60/869,930, filed on Dec. 14, 2006.

(51) Int. Cl.
C07D 473/18 (2006.01)
A61K 31/522 (2006.01)
A61P 11/06 (2006.01)
A61P 37/08 (2006.01)

(52) U.S. Cl. ............... 514/232.8; 514/234.2; 514/263.2; 514/263.22; 514/252.16; 514/263.37; 514/263.38; 544/81; 544/118; 544/276

(58) Field of Classification Search .............. 514/232.8, 514/234.5, 263.22, 236.37, 234.2, 252.16, 514/263.2; 544/81, 118, 276
See application file for complete search history.

(56) References Cited

U.S. PATENT DOCUMENTS

| | | | |
|---|---|---|---|
| 4,179,562 A | 12/1979 | Ponsford | |
| 4,689,338 A | 8/1987 | Gerster | |
| 4,698,348 A | 10/1987 | Gerster | |
| 4,714,701 A | 12/1987 | Beauchamp | |
| 4,912,112 A | 3/1990 | Seydel et al. | |
| 5,736,549 A | 4/1998 | Beasley et al. | |
| 5,994,361 A | 11/1999 | Penney et al. | |
| 6,028,076 A | 2/2000 | Hirota et al. | |
| 6,110,923 A | 8/2000 | Ely | |
| 6,329,381 B1 | 12/2001 | Kurimoto et al. | |
| 6,376,501 B1 | 4/2002 | Isobe et al. | |
| 6,448,236 B1 | 9/2002 | Monaghan | |
| 6,458,798 B1 | 10/2002 | Fujita et al. | |
| 6,630,478 B2 | 10/2003 | Diamond et al. | |
| 6,887,880 B2 | 5/2005 | Levy et al. | |
| 6,951,866 B2 | 10/2005 | Fujita et al. | |
| 7,157,465 B2 | 1/2007 | Isobe et al. | |
| 7,642,350 B2 * | 1/2010 | Pryde | 544/61 |
| 7,691,877 B2 | 4/2010 | Jones et al. | |
| 2002/0040032 A1 | 4/2002 | Glasky et al. | |
| 2002/0128264 A1 | 9/2002 | Taylor et al. | |
| 2003/0144283 A1 | 7/2003 | Coleman et al. | |
| 2003/0191086 A1 | 10/2003 | Hanus et al. | |
| 2003/0212092 A1 | 11/2003 | Heppner et al. | |
| 2004/0019048 A1 | 1/2004 | Crooks et al. | |
| 2004/0204438 A1 | 10/2004 | Crooks et al. | |
| 2004/0214192 A1 | 10/2004 | Hashida et al. | |
| 2004/0229897 A1 | 11/2004 | Crooks et al. | |
| 2005/0054590 A1 | 3/2005 | Averett et al. | |
| 2005/0119273 A1 | 6/2005 | Lipford et al. | |
| 2006/0052403 A1 | 3/2006 | Isobe et al. | |
| 2006/0252774 A1 | 11/2006 | Vatner et al. | |
| 2007/0190071 A1 * | 8/2007 | Kurimoto et al. | 424/184.1 |
| 2007/0225303 A1 | 9/2007 | Ogita et al. | |
| 2007/0249638 A1 | 10/2007 | Giorgio et al. | |
| 2008/0008682 A1 * | 1/2008 | Chong et al. | 424/85.6 |
| 2008/0269240 A1 * | 10/2008 | Hashimoto et al. | 514/252.16 |
| 2008/0300244 A1 * | 12/2008 | Bonnert et al. | 514/232.5 |
| 2009/0047249 A1 * | 2/2009 | Graupe et al. | 424/85.6 |
| 2009/0082332 A1 * | 3/2009 | Abbot et al. | 514/210.21 |
| 2009/0099216 A1 * | 4/2009 | Millichip et al. | 514/263.38 |
| 2009/0105212 A1 * | 4/2009 | Isobe et al. | 514/210.21 |
| 2009/0118263 A1 * | 5/2009 | Hashimoto et al. | 514/218 |
| 2009/0131458 A1 * | 5/2009 | Lazarides et al. | 514/263.23 |
| 2009/0143400 A1 * | 6/2009 | McInally et al. | 514/252.16 |

(Continued)

FOREIGN PATENT DOCUMENTS

| | | |
|---|---|---|
| CA | 1220148 | 4/1987 |
| CN | 101239980 | 8/2008 |
| EP | 1035123 | 8/2003 |
| EP | 1728793 | 12/2006 |
| EP | 1908480 | 4/2008 |

(Continued)

OTHER PUBLICATIONS

Chavarot, "Synthesis of an adenine-pyridinaldoxime-acridine conjugate for recognition of abasic site lesions in DNA," Tetrahedron, 1997, 53(40), pp. 13749-13756.

(Continued)

*Primary Examiner* — Mark Berch
(74) *Attorney, Agent, or Firm* — Morgan, Lewis & Bockius LLP

(57) ABSTRACT

The present invention provides compounds of formula

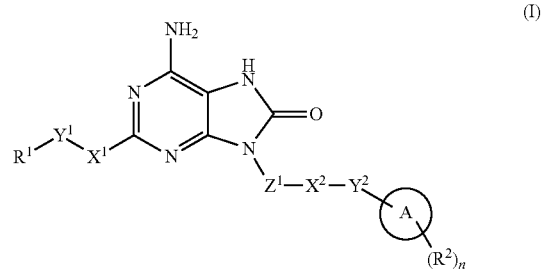

(I)

wherein $R^1, Y^1, X^1, Z^1, X^2, Y^2$, A, n and $R^2$ are as defined in the specification, processes for their preparation, pharmaceutical compositions containing them and their use in therapy.

12 Claims, No Drawings

U.S. PATENT DOCUMENTS

| | | | |
|---|---|---|---|
| 2009/0192153 A1* | 7/2009 | Hashimoto et al. | 514/234.2 |
| 2009/0202484 A1* | 8/2009 | Chong et al. | 424/85.6 |
| 2009/0209524 A1 | 8/2009 | Bennett et al. | |
| 2009/0281075 A1 | 11/2009 | Roughton et al. | |
| 2009/0324551 A1* | 12/2009 | Carson et al. | 424/93.4 |
| 2009/0325877 A1* | 12/2009 | Grunt et al. | 514/12 |
| 2010/0075995 A1* | 3/2010 | Biggadike et al. | 514/263.22 |
| 2010/0087443 A1* | 4/2010 | Bonnert et al. | 514/252.16 |
| 2010/0093998 A1* | 4/2010 | Isobe et al. | 540/575 |
| 2010/0099870 A1* | 4/2010 | Isobe et al. | 544/276 |
| 2010/0120799 A1* | 5/2010 | Lazarides et al. | 514/263.23 |
| 2010/0130491 A1* | 5/2010 | Bonnert et al. | 514/234.2 |
| 2010/0240623 A1* | 9/2010 | Cook et al. | 514/171 |
| 2010/0280001 A1 | 11/2010 | Bonnert et al. | |
| 2010/0298364 A1 | 11/2010 | Bennett et al. | |
| 2011/0028715 A1 | 2/2011 | Isobe et al. | |
| 2011/0054168 A1 | 3/2011 | Kurimoto et al. | |

FOREIGN PATENT DOCUMENTS

| | | |
|---|---|---|
| GB | 1375162 | 11/1974 |
| JP | 08-165292 | 6/1996 |
| JP | 347422/1997 | 11/1997 |
| JP | 367449/1997 | 12/1997 |
| JP | 367451/1997 | 12/1997 |
| JP | 10-501533 | 2/1998 |
| JP | 11-180981 | 7/1999 |
| JP | 11-180982 | 7/1999 |
| JP | 11-193282 | 7/1999 |
| JP | 2000-159767 | 6/2000 |
| JP | 2004-137157 | 5/2004 |
| JP | 2005-089334 | 4/2005 |
| WO | WO 99/5024 | 10/1999 |
| WO | WO 00/12487 | 3/2000 |
| WO | WO 00/76519 | 12/2000 |
| WO | WO 03/011864 | 2/2003 |
| WO | WO 2004/011481 | 2/2004 |
| WO | WO 2004/075865 | 9/2004 |
| WO | WO 2004/087049 | 10/2004 |
| WO | WO 2005/092892 | 10/2005 |
| WO | WO 2005/092893 | 10/2005 |
| WO | WO 2006/029115 | 3/2006 |
| WO | WO 2006/091394 | 8/2006 |
| WO | WO 2007/031726 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2007/093901 | 8/2007 |
| WO | WO 2008004948 A1 * | 1/2008 |
| WO | WO 2008/114006 | 9/2008 |
| WO | WO 2008/114008 | 9/2008 |
| WO | WO 2008/114817 | 9/2008 |
| WO | WO 2008/114819 | 9/2008 |
| WO | WO 2008/135791 | 11/2008 |
| WO | WO 2009067081 | 5/2009 |
| WO | WO 2009/078798 | 6/2009 |
| WO | WO 2009091031 | 7/2009 |
| WO | WO 2009091032 | 7/2009 |
| WO | WO 2010018131 A1 * | 2/2010 |
| WO | WO 2010018134 A1 * | 2/2010 |
| WO | WO 2010/033074 | 3/2010 |
| WO | WO 2010/133882 | 11/2010 |

OTHER PUBLICATIONS

Dvorakova, "Synthesis of 2'-aminomethyl derivatives of N-(2-(phosphonomethoxy)ethyl) nucleotide analogues as potential antiviral agents," J. Med. Chem., 1996, 39(17), pp. 3263-3268.

Hirota et al., "Discovery of 8-hydroxyadenines as a novel type of interferon inducer," J. Med. Chem., 2002, 45 (25), pp. 5419-5422.

Holy et al., "Studies on S-adenosyl-L-homocysteine hydrolase. XVI. 9-(Aminoalkyl)-8-hydroxyadenines: preparation mechanism of formation, and use in affinity chromatography of S-adenosyl-L-homocysteine hydrolase," Collection of Czechoslovak Chemical Communications (1986), 51(2), pp. 459-477.

Isobe et al., "Synthesis and structure-activity relationships of 2-substituted-8-hydroxyadenine derivatives as orally available interferon inducers without emetic side effects," Bioorganic & Medicinal Chemistry, 2003, 11(17), pp. 3641-3647.

Isobe, Y et al., "Synthesis and biological evaluation of novel 9-substituted-8-hydroxyadenine derivatives as potent interferon inducers," J. Med. Chem., 2006, 49 (6), pp. 2088-2095.

Itahara, "Control of liquid-crystalline properties by base pairing of adenine and thymine," ChemPhysChem, 2002, 3(4), pp. 378-379.

Kurimoto et al., "Prodrugs of 9-benzyl-8-hydroxy-2-(2-hydroxyethylthio)adenine: potent interferon inducing agents in monkeys," Chemical & Pharmaceutical Bulletin, 2004, 52(4), pp. 466-469.

Kurimoto et al., "Synthesis and biological evaluation of 8-oxoadenine derivatives as Toll-like Receptor 7 agonists introducing the antedrug concept," J. Med. Chem., 2010, 53, pp. 2964-2972.

Kurimoto et al., "Synthesis and evaluation of 2-substituted 8-hydroxyadenines as potent interferon inducers with improved oral bioavailabilities," Bioorganic & Medicinal Chemistry, 2004, 12(5), pp. 1091-1099.

Kurimoto et al., "Synthesis and structure-activity relationships of 2-amino-8-hydroxyadenines as orally active interferon inducing agents," Bioorganic & Medicinal Chemistry, 2003, 11(24), pp. 5501-5508.

Priority Document of WO 2009005687, (2007).

Spassova et al., "Synthesis of N-(3-Azido-2-hydroxypropyl), N-(3-Phthalimido-2-hydroxypropyl) and N-(3-Amino-2-hydroxypropyl) Derivatives of Heterocyclic Bases," Collection of Czechoslovak chemical Communications (1994), 59(5), 1153-1174.

"Asthma" (MDAdvice.com) retrieved on Jun. 24, 2010 from the internet (URL: http://www.mdadvice.com/topics/asthma/info/1.htm).

"Chronic obstructive pulmonary disease"(AllRefer.com Health) retrieved on Jun. 24, 2010 from the internet (URL: http://health.allrefer.com/health/chronic-obstructive-pulmonary-disease-prevention.html).

"Respiratory experts call for global approach to treat chronic diseases" (Feb.13, 2007) retrieved on Jun. 24, 2010 from the internet (URL: http://www.medwire-news.md/48/64443/Respiratory/Respiratory_experts_call_for_global_approach_to_treat_chronic_disease.html).

Aoki et al., "Weekly dosing of AZD8848/DSP-3025, A novel TLR7 agonist antedrug, demonstrates a prolonged period of control against markers of pulmonary inflammation in an alergen challenge model in the mouse" ATS International Conference, New Orleans, May 2010.

Bell et al., "AZD8848/DSP-3025, A novel potent TLR7 agonist antedrug, demonstrates negligible systemic activity and a prolonged period of control after cessation of weekly dosing in a brown norway rat ovalbumin challenge model" ATS International Conference, New Orleans, May 2010.

Biffen et al., "Biological activity of a novel TLR7 agonist antedrug for the treatment of allergic diseases," ATS International Conference, New Orleans, May 2010.

Drazen, "Surgery for emphysema — Not for everyone" New England Journal of Medicine, 345(15): 1126-1128 (2001).

Falco et al., "2,4-Diaminopyrimidines as antimalarials. i.1 5-aryloxyl and 5-alkoxyl derivatives," Journal of the American Chemical Society 73(8): 3753-3758 (1951).

Fridkin, "Vancomycin-intermediate and —resistant staphylococcus aureus: what the infectious disease specialist needs to know," Clinical Infectious diseases, Society for Healthcare Epidemiology of America, 32: 108-115 (2001).

Ikeda et al., "AZD8848/Dsp-3025, A novel potent TLR7 agonist antedrug, demonstrates efficacy against airway obstruction and other inflammatory endpoints in guinea pig models of rhinitis and asthma with acute and weekly dosing" ATS International Conference, New Orleans, May 2010.

Korc, "Pathways for aberrant angiogenesis in pancreatic cancer," Molecular Cancer, Biomed Central, 2(8): 1-8 (2003).

Krueger et al., "Tilorone hydrochloride: An orally active antiviral agent," Science, 169: 1213-1214 (1970).

Laino, "In small study, imaging detects lung damage in people exposed to secondhand smoke," Oncology Times, 30(2): 15 (Jan. 25, 2008).

Lee et al., "Activation of anti-hepatitis C 1-17, 21-22 virus responses via Toll-like receptor 7," Proc. Natl. Acad. Sci. USA, 103(6):1828-1833 (2006).

Lee et al., "Molecular basis for the immunostimulatory activity of guanine nucleoside analogs: Activation of Toll-like receptor 7," Proc. Natl. Acad. Sci. USA, 100(11):6646-6651 (2003).

Matsui et al., "Mechanisms of inhibition of type-2 cytokines by novel TLR7 agonist antedrugs," ATS International Conference, New Orleans, May 2010.

Mayer et al., "Tilorone hydrochloride: Mode of acton," Science, 169:1214-1215 (1970).

McInally "Identification and pharmacology of novel TLR7 agonist antedrugs," RSC BMSC Inflammation meeting, Nov. 18, 2010.

McInally et al., "Identification of a novel TLR7 agonist antedrug," EFMC-ISMC 2010, 21st International Symposium on Medicinal Chemistry, Brussels, Belgium, Sep. 5-9, 2010.

Mogulkoc et al., "Pulmonary function in idiopathic pulmonary fibrosis and referral for lung transplantation," American Journal of Respiratory and Critical Care Medicine, 164(1): 103-108 (2001).

Nichol et al., "Stimulation of murine interferon by a substituted pyrimidine," Antimicrobial Agents and Chemotherapy, 9(3): 433-439 (1976).

Palmer et al., "Highly drug-resistant HIV-1 clinical isolates are cross-resistant to many antiretroviral compounds in current clinical development," AIDS, Lippincott Williams & Wilkins, 13(6): 661-667 (1999).

Reiter et al., "Cytokine induction in mice by the immunomodulator imiquimod," Journal of Leukocyte Biology, 55: 234-240 (1994).

Stringfellow et al., "Antiviral and interferon-inducing properties of 1,5-diamino anthraquinones," Antimicrobial Agents and Chemotherapy, 15(1): 111-118 (1979).

Tarkoy et al., "Nucleic-acid analogues with constraint conformational flexibility in the sugar-phosphate backbone ('Bicyclo-DNA')," Helvetica Chimica Acta, 76(1): 481-510 (1993).

Tojo et al., "Synthesis and biological evaluation of a novel TLR7 agonist with an antedrug strategy," EFMC-ISMC 2010, 21st International Symposium on Medicinal Chemistry, Brussels, Belgium, Sep. 5-9, 2010.

Yoshimoto et al., "Correlation analysis of Baker's studies on enzyme inhibition. 2. Chymotrypsin, trypsin, thymidine phosphorylase, uridine phosphorylase, thymidylate synthetase, cytosine nucleoside deaminase, dihydrofolate reductase, malate dehydrogenase, glutamate dehydrogenase, lactate dehydrogenase, and glyceraldehyde-phosphate dehydrogenase," Journal of Medicinal Chemistry, 19(1): 71-98 (1976).

Zalutsky, "Targeted radiotherapy of brain tumors," British Journal of Cancer, 90: 1469-1473 (2004).

* cited by examiner

COMPOUNDS

CROSS-REFERENCE TO RELATED APPLICATIONS

RELATED APPLICATIONS

The present application claims the benefit of U.S. Provisional Patent Application Ser. No. 60/869,930, filed Dec. 14, 2006, which is hereby incorporated by reference in its entirety.

NAMES OF PARTIES TO A JOINT RESEARCH AGREEMENT

The subject matter claimed in this application was made as a result of activities undertaken within the scope of a joint research agreement dated Dec. 19, 2003, between AstraZeneca AB and Sumitomo Pharmaceuticals Co., Ltd. All of the rights and obligations of Sumitomo Pharmaceuticals Co., Ltd. as defined in the joint research agreement between AstraZeneca AB and Sumitomo Pharmaceuticals Co., Ltd. were assumed by Dainippon Sumitomo Pharma Co., Ltd., a company created by the merger of Dainippon Pharmaceuticals Co., Ltd. and Sumitomo Pharmaceuticals Co., Ltd. effective Oct. 3, 2005.

BACKGROUND OF THE INVENTION

The present invention relates to adenine derivatives, processes for their preparation, pharmaceutical compositions containing them and their use in therapy.

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha(IFNα)) and upregulation of co-stimulatory molecules on phagocytes, leading to modulation of T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRR, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in WO 98/01448 and WO 99/28321.

This patent application describes a class of 9-substituted-8-oxoadenine compounds having immuno-modulating properties which act via TLR7 that are useful in the treatment of viral or allergic diseases and cancers.

In accordance with the present invention, there is therefore provided a compound of formula (I):

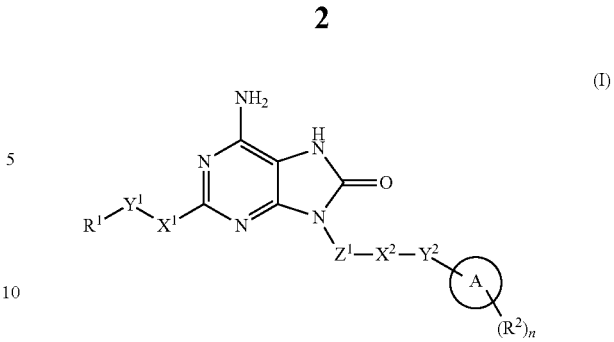

wherein $R^1$ represents hydrogen, hydroxyl, $C_1$-$C_6$ alkoxy, $C_2$-$C_5$ alkoxycarbonyl, $C_1$-$C_6$ haloalkyl, $C_1$-$C_6$ haloalkoxy, or a $C_6$-$C_{10}$ aryl, $C_5$-$C_{10}$ heteroaryl or $C_3$-$C_8$ cycloalkyl group, each group being optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, $C_2$-$C_5$ alkoxycarbonyl, amino ($NH_2$) and di-$C_1$-$C_6$ alkylamino;

$Y^1$ represents a single bond or $C_1$-$C_6$ alkylene;

$X^1$ represents a single bond or an oxygen or sulphur atom or sulphonyl ($SO_2$) or $NR^3$;

$Z^1$ represents a $C_2$-$C_6$ alkylene or $C_3$-$C_8$ cycloalkylene group, each of which may be optionally substituted by at least one hydroxyl;

$X^2$ represents $NR^4$, $CONR^4$, $NR^4CO$, $SO_2NR^4$, $NR^4CONR^5$ or $NR^5CONR^4$, $SO_2$, $CO$, $NR^5CSNR^5$;

$Y^2$ represents a single bond or $C_1$-$C_6$ alkylene;

n is an integer 0, 1 or 2;

each $R^2$ group independently represents halogen, cyano, $S(O)_mR^9$, $OR^{10}$, $SO_2NR^{10}R^{11}$, $CONR^{10}R^{11}$, $NR^7R^8$, $NR^{10}SO_2R^9$, $NR^{10}CO_2R^9$, $NR^{10}COR^9$, $C_6$-$C_{10}$ aryl, $C_5$-$C_{10}$ heteroaryl group, $C_1$-$C_6$ alkyl, $C_2$-$C_6$ alkenyl, $C_2$-$C_6$ alkynyl or $C_3$-$C_8$ cycloalkyl group, the latter six groups being optionally substituted by one or more substituents independently selected from halogen, cyano, $S(O)_mR^{12}$, $OR^{13}$, $SO_2NR^{13}R^{14}$, $CONR^{13}R^{14}$, $NR^7R^8$, $NR^{13}SO_2R^{12}$, $NR^{13}CO_2R^{12}$, $NR^{13}COR^{12}$, $C_1$-$C_6$ alkyl or $C_3$-$C_8$cycloalkyl $R^3$ represents hydrogen or $C_1$-$C_6$ alkyl;

$R^4$ represents hydrogen or a 3- to 8-membered saturated heterocyclic ring comprising a ring group O or $NR^6$;

or $R^4$ represents a $C_1$-$C_6$ alkylene optionally substituted by one or more substituents independently selected from $NR^7R^8$ or $R^6$;

$R^5$ represents hydrogen or a $C_1$-$C_6$ alkyl or $C_3$-$C_6$ cycloalkyl group, each of which may be optionally substituted by one or more substituents independently selected from halogen, hydroxyl and $NR^7R^8$;

$R^6$ represents hydrogen, $CO_2R^9$, $SO_2R^9$, $COR^9$, $SO_2NR^{10}R^{11}$, $CONR^{10}R^{11}$, a 3- to 8-membered saturated heterocyclic ring comprising a ring group $NR^9$; or (i) a $C_6$-$C_{10}$ aryl or $C_5$-$C_{10}$ heteroaryl group, each of which may be optionally substituted by one or more substituents independently selected from halogen, cyano, oxo, carboxyl, $S(O)_mR^{12}$, $OR^{13}$, $SO_2NR^{13}R^{14}$, $CONR^{13}R^{14}$, $NR^{13}R^{14}$, $NR^{13}SO_2R^{12}$, $NR^{13}CO_2R^{12}$, $NR^{13}COR^{12}$, $C_1$-$C_6$ alkyl and $C_1$-$C_3$ haloalkyl, or (ii) a $C_1$-$C_6$ alkyl, $C_2$-$C_6$ alkenyl, $C_2$-$C_6$ alkynyl or $C_3$-$C_8$ cycloalkyl group, each of which may be optionally substituted by one or more substituents independently selected from halogen, cyano, $C_3$-$C_8$ cycloalkyl, $OR^{15}$, $S(O)_pR^{16}$, $CO_2R^{16}$, $NR^{17}R^{18}$, $CONR^{17}R^{18}$, $NR^{17}COR^{16}$, $SO_2NR^{17}R^{18}$, $NR^{17}SO_2R^{16}$ and a group as defined in (i) above;

$R^7$, $R^8$, $R^{13}$, $R^{14}$ $R^{15}$, $R^{19}$, $R^{22}$, $R^{23}$, $R^{24}$ and $R^{25}$ each independently represent hydrogen, $C_1$-$C_6$ alkyl or $C_3$-$C_6$ cycloalkyl;

or $R^7$ and $R^8$ together with the nitrogen atom to which they are attached form a 3- to 8-membered saturated heterocyclic ring comprising a ring nitrogen atom and optionally one or more further heteroatoms independently selected from nitrogen, oxygen, sulphur and sulphonyl, the heterocyclic ring being optionally substituted by one or more substituents independently selected from halogen, hydroxyl, carboxyl, cyano, $OR^{21}$, $S(O)_qR^{21}$, $NR^{22}R^{23}$, $C_1$-$C_6$ alkyl and $C_3$-$C_8$ cycloalkyl;

$R^9$, $R^{16}$ and $R^{21}$ each independently represent a $C_1$-$C_6$ alkyl or $C_3$-$C_6$ cycloalkyl group, each of which may be optionally substituted by one or more substituents independently selected from halogen, carboxyl, hydroxyl and $NR^{19}R^{20}$;

either $R^{10}$ represents hydrogen or a $C_1$-$C_6$ alkyl, $C_2$-$C_6$ alkenyl, $C_2$-$C_6$ alkynyl or $C_3$-$C_8$ cycloalkyl group, each of which may be optionally substituted by one or more substituents independently selected from halogen, hydroxyl, carboxyl, cyano, $OR^{21}$, $S(O)_qR^{21}$, $NR^{22}R^{23}$ and $C_3$-$C_8$ cycloalkyl, and $R^{11}$ represents hydrogen or a $C_1$-$C_6$ alkyl or $C_3$-$C_6$ cycloalkyl group, each of which may be optionally substituted by one or more substituents independently selected from halogen, hydroxyl and $NR^{24}R^{25}$, or $R^{10}$ and $R^{11}$ together with the nitrogen atom to which they are attached form a 3- to 8-membered saturated heterocyclic ring comprising at least one heteroatom or heterogroup selected from nitrogen, oxygen, sulphur and sulphonyl, the heterocyclic ring being optionally substituted by one or more substituents independently selected from halogen, hydroxyl, carboxyl, cyano, $OR^{21}$, $S(O)_qR^{21}$, $NR^{22}R^{23}$, $C_1$-$C_6$ alkyl and $C_3$-$C_8$ cycloalkyl;

$R^{12}$ represents $C_1$-$C_6$ alkyl or $C_3$-$C_6$ cycloalkyl;

$R^{17}$ and $R^{18}$ are defined as for $R^{10}$ and $R^{11}$ respectively;

m, p and q each independently represent an integer 0, 1 or 2; and

A represents a monocyclic or bicyclic $C_6$-$C_{10}$ aryl or a monocyclic or bicyclic $C_5$-$C_{12}$ heteroaryl group containing 1-3 heteroatoms;

or a pharmaceutically acceptable salt thereof.

In the context of the present specification, unless otherwise stated, an alkyl substituent group or an alkyl moiety in a substituent group may be linear or branched. Examples of $C_1$-$C_6$ alkyl groups/moieties include methyl, ethyl, n-propyl, isopropyl, n-butyl, isobutyl, tert-butyl, n-pentyl and n-hexyl. Similarly, an alkylene group/moiety may be linear or branched. Examples of $C_1$-$C_6$ alkylene groups/moieties include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene. A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl. The alkyl groups in a di-$C_1$-$C_6$ alkylamino or alkylcarbonyl group/moiety may be the same as, or different from, one another. A $C_1$-$C_6$ hydroxyalkyl or $C_1$-$C_6$ hydroxyalkoxy substituent group/moiety will comprise at least one hydroxyl group, e.g. one, two or three hydroxyl groups. An aryl or heteroaryl substituent group/moiety may be monocyclic or polycyclic (e.g. bicyclic or tricyclic) in which the two or more rings are fused. A heteroaryl group/moiety will comprise at least one ring heteroatom (e.g. one, two, three or four ring heteroatoms independently) selected from nitrogen, oxygen and sulphur. Examples of aryl and heteroaryl groups/moieties include phenyl, 1-naphthyl, 2-naphthyl, furyl, thienyl, pyrrolyl, pyridyl, indolyl, isoindolyl, quinolyl, isoquinolyl, pyrazolyl, imidazolyl, pyrimidinyl, pyrazinyl, pyridazinyl, thiazolyl and oxazolyl.

A $C_2$-$C_{10}$ acyloxy group/moiety is exemplified by a $C_2$-$C_5$ alkylcarbonyloxy group, a $C_2$-$C_5$ alkenylcarbonyloxy group, a $C_2$-$C_5$ alkynylcarbonyloxy group, a $C_6$-$C_9$ arylcarbonyloxy group or a $C_5$-$C_9$ heteroarylcarbonyloxy group, each of which may be optionally substituted by one or more substituents independently selected from halogen, hydroxyl, $C_1$-$C_3$ alkoxy or phenyl ring, optionally substituted by from halogen, hydroxyl, cyano, $OR^{21}$, $S(O)_qR^{21}$ or $C_1$-$C_6$ alkyl, providing that the total number of carbon atoms in the acyloxy group does not exceed 10.

Preferably $R^1$ represents hydrogen.
Preferably $Y^1$ represents $C_1$-$C_6$ alkylene, more preferably $C_4$ alkylene
Preferably $X^1$ represents oxygen
Preferably $Z^1$ represents $C_2$-$C_6$ alkylene, more preferably $(CH_2)_3$.
Preferably $X^2$ represents $NR^4$.
Preferably $Y^2$ represents $C_1$-$C_6$ alkylene, more preferably a $CH_2$ group.
Preferably A represents phenyl
Preferably $R^2$ is hydrogen or $C_1$-$C_6$ alkoxy
Examples of compounds of the invention include:
6-Amino-9-{3-[benzyl(3-morpholin-4-ylpropyl)amino]propyl}-2-butoxy-7,9-dihydro-8H-purin-8-one
6-Amino-2-butoxy-9-{3-[(4-isopropoxybenzyl)(3-morpholin-4-ylpropyl)amino]propyl}-7,9-dihydro-8H-purin-8-one
6-Amino-2-butoxy-9-{3-[(4-methoxybenzyl)(3-morpholin-4-ylpropyl)amino]propyl}-7,9-dihydro-8H-purin-8-one
6-Amino-2-butoxy-9-{3-[(2,3-dihydro-1,4-benzodioxin-6-ylmethyl)(3-morpholin-4-ylpropyl)amino]propyl}-7,9-dihydro-8H-purin-8-one
6-Amino-2-butoxy-9-{3-[(3,4-dimethoxybenzyl)(3-morpholin-4-ylpropyl)amino]propyl}-7,9-dihydro-8H-purin-8-one
6-Amino-2-butoxy-9-{3-[(4-morpholin-4-ylbenzyl)(3-morpholin-4-ylpropyl)amino]propyl}-7,9-dihydro-8H-purin-8-one
6-Amino-2-butoxy-9-{3-[(3-morpholin-4-ylpropyl)(4-pyrimidin-2-ylbenzyl)amino]propyl}-7,9-dihydro-8H-purin-8-one
6-Amino-2-butoxy-9-{3-[[4-(methylthio)benzyl](3-morpholin-4-ylpropyl)amino]propyl}-7,9-dihydro-8H-purin-8-one
6-Amino-2-butoxy-9-(3-{(3-morpholin-4-ylpropyl) [(2-oxo-2H-chromen-6-yl)methyl]amino}propyl)-7,9-dihydro-8H-purin-8-one
6-Amino-2-butoxy-9-(3-{(3-morpholin-4-ylpropyl) [(2-oxo-2,3-dihydro-1,3-benzothiazol-6-yl)methyl]amino}propyl)-7,9-dihydro-8H-purin-8-one 6-Amino-2-butoxy-9-{3-[(3-morpholin-4-ylpropyl)(4-propoxybenzyl)amino]propyl}-7,9-dihydro-8H-purin-8-one 6-Amino-2-butoxy-9-{3-[(3,5-dimethoxybenzyl)(3-morpholin-4-ylpropyl)amino]propyl}-7,9-dihydro-8H-purin-8-one 6-Amino-2-butoxy-9-{3-[(2,4-dimethoxybenzyl)(3-morpholin-4-ylpropyl)amino]propyl}-7,9-dihydro-8H-purin-8-one (4-{[[3-(6-Amino-2-butoxy-8-oxo-7,8-dihydro-9H-purin-9-yl)propyl](3-morpholin-4-ylpropyl)amino]methyl}phenoxy)acetonitrile 6-Amino-2-butoxy-9-{3-[(3-morpholin-4-ylpropyl)(4-pyrrolidin-1-ylbenzyl)amino]propyl}-7,9-dihydro-8H-purin-8-one 6-Amino-2-butoxy-9-(3-{(3-morpholin-4-ylpropyl)[4-(1H-1,2,4-triazol-1-yl)benzyl]amino}propyl)-7,9-dihydro-8H-purin-8-one 6-Amino-2-butoxy-9-{3-[[4-(methylsulfonyl)benzyl](3-morpholin-4-ylpropyl)amino]propyl}-7,9-dihydro-8H-purin-8-one 4-{[[3-(6-Amino-2-butoxy-8-oxo-7,8-dihydro-9H-purin-9-yl)propyl](3-morpholin-4-ylpropyl)amino]methyl}-N-(tert-butyl)benzenesulfonamide 6-Amino-2-butoxy-9-{3-[[4-(hydroxymethyl)benzyl](3-morpholin-4-ylpropyl)amino]propyl}-7,9-dihydro-8H-purin-8-one 6-Amino-9-(3-{benzyl[2-(dimethylamino)ethyl]amino}propyl)-2-butoxy-7,9-dihydro-8H-purin-8-one 6-Amino-9-{3-[benzyl(1-methylpiperidin-4-yl)amino]propyl}-2-butoxy-7,9-dihydro-8H-purin-8-one and pharmaceutically acceptable salts or solvates thereof.

The present invention further provides a process for the preparation of a compound of formula (I).

The present invention further provides a process for the preparation of a compound of formula (I) or a pharmaceutically acceptable salt thereof as defined above which comprises, (a) reacting a compound of formula

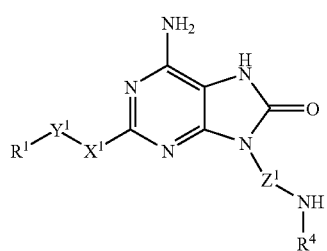

(II)

wherein $Z^1$, $Y^1$, $X^1$, $R^1$ and $R^4$ are as defined in formula (I), with a compound of formula

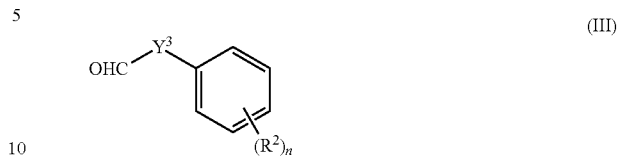

(III)

wherein $Y^3$ represents a bond or $C_1$-$C_5$ alkylene group and n and $R^2$ are as defined in formula (I) in the presence of a suitable reducing agent (e.g. sodium triacetoxyborohydride); or (b) reacting a compound of formula (II) as defined in (a) above with a compound of formula

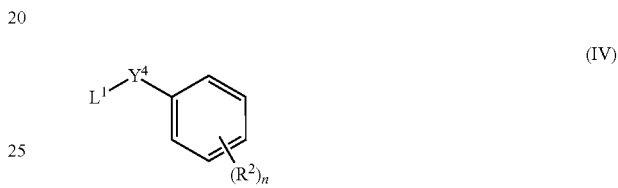

(IV)

wherein $Y^4$ represents $C_1$-$C_5$ alkylene group; $L^1$ represents a leaving group (e.g. halogen, mesylate or triflate) and n and $R^2$ are as defined in formula (I) in the presence of a suitable base (e.g. sodium carbonate or potassium carbonate), and optionally after carrying out one or more of the following:

converting the compound obtained to a further compound of the invention, removal of any protecting groups, forming a pharmaceutically acceptable salt of the compound; or In process (a), the reaction may conveniently be carried out in an organic solvent such as 1-methyl-2-pyrrolidinone, 1,2-dichloroethane or tetrahydrofuran at a temperature, for example, in the range from 0 to 150° C.

In process (b), the reaction may conveniently be carried out in an organic solvent such as acetonitrile, 1-methyl-2-pyrrolidinone or N,N-dimethylformamide at a temperature, for example, in the range from 0 to 150° C.

Compounds of formula (II) where $R^1$ represents hydrogen, $Y^1$ represents $C_1$-$C_6$ alkylene, and $X^1$ represents oxygen may be prepared as illustrated in the following reaction scheme:

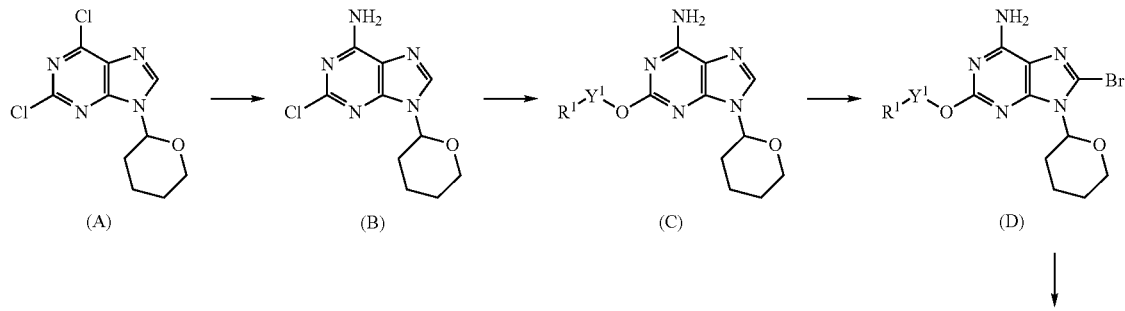

(A)     (B)     (C)     (D)

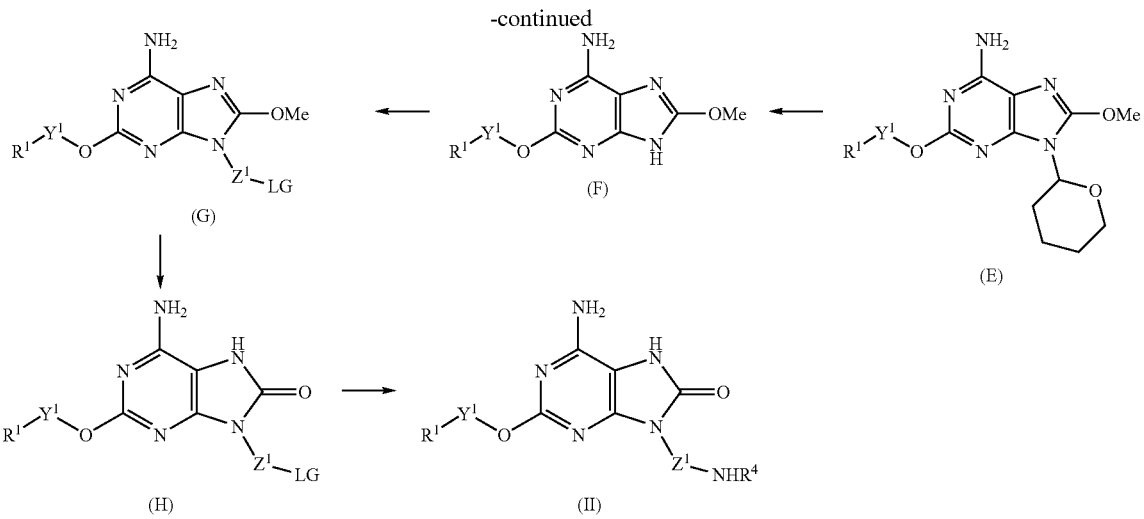

The compound of formula (B) is prepared by reacting the compound of formula (A) with ammonia in an organic solvent such as methanol, ethanol, propanol, butanol, tetrahydrofuran, 1,4-dioxane, diglyme, acetonitrile or an aqueous mixture of any one of the preceding solvents. The reaction may be carried out in an autoclave, and at a temperature, for example, in the range from 20 to 200° C.

Compounds of formula (C) may be prepared by reacting the compound of formula (B) with an alkanol in the presence of a base such as sodium hydride and in an organic solvent such as tetrahydrofuran, 1,4-dioxane, diglyme, N,N-dimethylformamide or dimethylsulfoxide, preferably at elevated temperature, e.g. at a temperature in the range from 20 to 150° C. Alternatively an alkali metal such as sodium may be dissolved in the alkanol and then reacted with the compound of formula (B), preferably at elevated temperature, e.g. at a temperature in the range from 20 to 150° C.

Compounds of formula (D) are prepared by brominating a compound of formula (C). The reaction may be carried out using a brominating agent such as bromine, hydroperbromic acid or N-bromosuccinimide, in an organic solvent such as carbon tetrachloride, methylene chloride, dichloroethane, diethyl ether, acetic acid or carbon disulfide. The reaction temperature will generally be in the range from 0° C. to the boiling point of the solvent.

Compounds of formula (E) are prepared by reacting a compound of formula (D) with sodium methoxide in an organic solvent such as methanol and at a temperature, for example, in the range from 20 to 150° C.

Compounds of formula (F) may be obtained by treating a compound of formula (E) with an acid such as trifluoroacetic acid in an organic solvent such as methanol.

Compounds of formula (G) are prepared by reacting a compound of formula (F) with a compound of formula LG-$Z^1$-LG wherein LG represents a leaving group such as a halogen, mesylate or triflate and $Z^1$ represents a $C_2$-$C_6$ alkylene group as defined in formula (II). The reaction may be carried out in an organic solvent such as N,N-dimethylformamide, dimethylsulfoxide or acetonitrile with a base present, preferably at room temperature (20° C.). A base such as an alkali metal carbonate, e.g. sodium carbonate or potassium carbonate; an alkaline earth metal carbonate, e.g. calcium carbonate; a metal hydroxide, e.g. sodium hydroxide or potassium hydroxide; a metal hydrogenate, e.g. sodium hydride; or a metal alkoxide, e.g. potassium t-butoxide, may be used.

Compounds of formula (H) may be obtained by treatment of a compound of formula (G) with an acid. The reaction may be carried out in an organic solvent such as methanol using either an inorganic acid such as hydrochloric acid, hydrobromic acid or sulfuric acid, or an organic acid such as trifluoroacetic acid.

Compounds of formula (II) are prepared by reacting a compound of formula (H) with an amine of formula $R^4NH_2$ where $R^4$ is as defined in formula (I). The reaction may be carried out in an organic solvent such as acetonitrile or N,N-dimethylformamide using an excess of the amine, preferably at elevated temperature, e.g. at a temperature in the range from 0 to 150° C.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, trifluoroacetate, sulphate, phosphate, acetate, fumarate, maleate, tartrate, lactate, citrate, pyruvate, succinate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as modulators of toll-like receptor (especially TLR7) activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, *molluscum contagiosum*, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, chlamydia, candida, *aspergillus*, cryptococcal meningitis, *pneumocystis carnii*, cryptosporidiosis, histoplasmosis, toxoplasmosis, trypanosome infection and leishmaniasis.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the invention may be used in the treatment of asthma, COPD, allergic rhinitis, allergic conjunctivitis, atopic dermatitis, cancer, hepatitis B, hepatitis C, HIV, HPV, bacterial infections and dermatosis.

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux®, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin α$_v$β3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention still further provides a method of treating, or reducing the risk of, an obstructive airways disease or condition (e.g. asthma or COPD) which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention (including pharmaceutically acceptable salts) may be administered by oral or nasal inhalation. For inhalation, the compound is desirably finely divided. The finely divided compound preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the abovementioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The invention therefore further relates to combination therapies wherein a compound of the invention or a pharmaceutical composition or formulation comprising a compound of the invention is administered concurrently or sequentially or as a combined preparation with another therapeutic agent or agents, for the treatment of one or more of the conditions listed.

In particular, for the treatment of the inflammatory diseases COPD, asthma and allergic rhinitis the compounds of the invention may be combined with agents such as tumour necrosis factor alpha (TNF-alpha) inhibitors such as anti-TNF monoclonal antibodies (for example infliximab [Remicade®], CDP-870 and adalimumab) and TNF receptor immunoglobulin molecules (such as entanercept [Enbrel®]); non-selective cyclo-oxygenase COX-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); glucocorticosteroids (whether administered by topical, oral, intramuscular, intravenous, or intra-articular routes); methotrexate, lefunomide; hydroxychloroquine, d-penicillamine, auranofin or other parenteral or oral gold preparations.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott®-79175; Abbott®-85761; a N-(5-substituted)-thiophene-2-alkylsulfonamide; 2,6-di-tert-butylphenolhydrazones; a methoxytetrahydropyrans such as Zeneca® ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LT B4, LTC4, LTD4, and LTE4) selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention and an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

The present invention still further relates to the combination of a compound of the invention together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present invention further relates to the combination of a compound of the invention and a chromone, such as sodium cromoglycate or nedocromil sodium.

The present invention still further relates to the combination of a compound of the invention together with an insulin-like growth factor type I (IGF-1) mimetic.

The present invention still further relates to the combination of a compound of the invention and a glucocorticoid, such as flunisolide, triamcinolone acetonide, beclomethasone dipropionate, budesonide, fluticasone propionate, ciclesonide or mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12.

The present invention still further relates to the combination of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX3CR1 for the C—X3-C family.

The present invention still further relates to the combination of a compound of the invention together with a cytokine or modulator of cytokine function, including alpha-, beta-, and gamma-interferon; interleukins (IL) including IL1 to 15, and interleukin antagonists or inhibitors, including agents which act on cytokine signalling pathways.

The present invention still further relates to the combination of a compound of the invention together with an immunoglobulin (Ig) or Ig preparation or an antagonist or antibody modulating Ig function such as anti-IgE (omalizumab).

The present invention further relates to the combination of a compound of the invention and another systemic or topically-applied anti-inflammatory agent, such as thalidomide or a derivative thereof, a retinoid, dithranol or calcipotriol.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamivir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin $α_vβ_3$ function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The present invention will be further explained by reference to the following illustrative examples.

The following abbreviations are used;

| | |
|---|---|
| EtOAc | ethyl acetate |
| DCM | dichloromethane |
| NMP | N-methylpyrrolidine |
| NBS | N-bromosuccinamide |
| DMF | N, N-dimethylformamide |
| DMSO | dimethylsulfoxide |
| THF | tetrahydrofuran |
| TFA | trifluoroacetic acid |
| mcpba | 3-chloroperoxybenzoic acid (Aldrich 77% max) |
| rt | room temperature |
| h | hours |
| min | minutes |
| M | molar |
| MS | mass spectrometry |
| APCI | atmospheric pressure chemical ionisation |
| NMR | nuclear magnetic resonance |
| HCl | hydrochloric acid |
| BOC | tertiary-butoxycarbonyl |
| HOBt | 1-hydroxybenzotriazole |
| EDC | 1-(3-dimethylamino propyl)-3-ethylcarbodiimide hydrochloride |
| HATU | O-(7-azabenzotriazol-1-yl)-N, N, N', N'-tetramethyluronium hexafluorophosphonate |

Unless otherwise stated organic solutions were dried over magnesium sulphate. RPHPLC denotes Reverse Phase Preparative High Performance Liquid Chromatography using Waters® Symmetry® C8, XTerra® or Phenomenex® Gemini™ columns using acetonitrile and either aqueous ammonium acetate, ammonia, formic acid or trifluoroacetic acid as buffer where appropriate. Column chromatography was carried out on silica gel. SCX denotes solid phase extraction with a sulfonic acid sorbent whereby a mixture was absorbed on a sulfonic acid sorbent and eluted with an appropriate solvent such as methanol or acetonitrile and then the free base product was eluted with aqueous ammonia/an appropriate solvent such as methanol or acetonitrile.

Biological Assay

Human TLR7 Assay

Recombinant human TLR7 was stably expressed in a HEK293 cell line already stably expressing the pNiFty2-SEAP reporter plasmid; integration of the reporter gene was maintained by selection with the antibiotic zeocin. The most common variant sequence of human TLR7 (represented by the EMBL sequence AF240467) was cloned into the mammalian cell expression vector pUNO and transfected into this reporter cell-line. Transfectants with stable expression were selected using the antibiotic blasticidin. In this reporter cell-line, expression of secreted alkaline phosphatase (SEAP) is controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the log of the minimal effective concentration of compound to induce SEAP release (pMEC).

| Compound of Example: | 8 | pMEC | 7.2 |
|---|---|---|---|
| | 12 | | >7.7 |
| | 16 | | 7.4 |

EXPERIMENTAL

Unless otherwise stated organic solutions were dried over magnesium sulphate. RPHPLC means reversed phase preparative HPLC using Waters® Symmetry® C8, XTerra® or Phenomenex® Gemini™ columns using acetonitrile and either aqueous ammonium acetate, ammonia, formic acid or trifluoroacetic acid as buffer where appropriate. Column chromatography was carried out on silica gel. Treating with SCX means the mixture was absorbed on SCX and eluted with an appropriate solvent such as methanol or acetonitrile then the free base product eluted with aqueous ammonia/methanol.

Example 1

6-Amino-9-{3-[benzyl(3-morpholin-4-ylpropyl)amino]propyl}-2-butoxy-7,9-dihydro-8H-purin-8-one

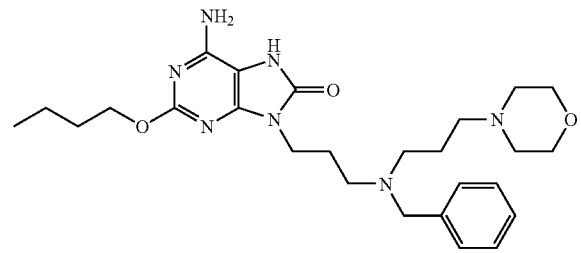

(i) 2-Chloro-9-(tetrahydro-2H-pyran-2-yl)-9H-purin-6-amine 2,6-Dichloro-9-(tetrahydro-2H-pyran-2-yl)-9H-purine (55 g) was dissolved in 7N-aqueous ammonia in methanol (500 ml) and heated at 100° C. in a sealed flask for 6 hours. The reaction mixture was cooled to room temperature and left overnight. Filtration afforded the subtitle compound. Yield 40 g.

$^1$H NMR δ (CDCl$_3$) 8.02 (1H, s), 5.94 (2H, brs), 5.71 (1H, dd), 4.15-4.22 (1H, m), 3.75-3.82 (1H, m), 1.27-2.12 (6H, m).

(ii) 2-Butoxy-9-(tetrahydro-2H-pyran-2-yl)-9H-purin-6-amine

The product from step (i) (40 g) was dissolved in 19% (w/w)-sodium butoxide in butanol (250 ml). The reaction mixture was stirred under reflux for 6 hours. The resultant suspension was cooled to room temperature, diluted with water and extracted with diethyl ether. The combined organic phase was washed with water, dried and concentrated in vacuo. The subtitle compound was crystallised from diethyl ether/isohexane (1/1, 300 ml) and obtained by filtration. Yield 19 g.

$^1$H NMR δ (CDCl$_3$) 7.87 (1H, s), 5.56-5.68 (3H, m), 4.31-4.35 (2H, t), 4.14-4.17 (1H, m), 3.76-3.80 (1H, m), 1.49-2.08 (10H, m), 0.98 (3H, t).

(iii) 8-Bromo-2-butoxy-9-(tetrahydro-2H-pyran-2-yl) 9H-purin-6-amine

The product from step (ii) (30 g) was dissolved in dry dichloromethane (200 ml). The solution was stirred at room temperature whilst N-bromosuccinamide (27 g) was added portionwise. The mixture was stirred at ambient temperature overnight. 20% (w/v)-Sodium sulfate (200 ml) was added and the separated aqueous phase extracted with dichloromethane. The combined organic phase was washed with saturated sodium hydrogen carbonate solution and brine. After concentration in vacuo, the residue was dissolved in ethyl acetate, washed with water, brine and dried. The solution was filtered through silica gel and concentrated in vacuo. The residue was triturated with diethyl ether and isohexane (1/1, 200 ml) then filtered to give the subtitle compound (26 g). The filtrate was concentrated in vacuo and the residue purified by column chromatography (ethyl acetate/isohexane) to give a further 2.5 g of product. The solids were combined to give the subtitle compound as a yellow solid. Yield 28.5 g. mp 148-50° C.

$^1$H NMR δ (CDCl$_3$) 5.59-5.64 (3H, m), 4.32 (2H, m), 4.17 (1H, m), 3.74 (1H, m), 3.08 (1H, m), 2.13 (1H, d), 1.48-1.83 (8H, m), 0.98 (3H, t).

(iv) 2-Butoxy-8-methoxy-9-(tetrahydro-2H-pyran-2-yl)9H-purin-6-amine

Sodium (3.7 g) was added to absolute methanol (400 ml) under a nitrogen atmosphere. To this solution was added the product from step (iii) (28.5 g) and the mixture was stirred at 65° C. for 9 hours. The mixture was concentrated in vacuo and 500 ml of water added. The aqueous phase was extracted with ethyl acetate, washed with brine and dried. The subtitle compound was obtained after crystallisation from diethyl ether. Yield 14.2 g.

$^1$H NMR δ (CDCl$_3$) 5.51 (1H, dd), 5.28 (2H, brs), 4.29 (2H, t), 4.11-4.14 (4H, m), 3.70 (1H, m), 2.76-2.80 (1H, m), 2.05 (1H, d), 1.47-1.81 (8H, m), 0.97 (3H, t).

(v) 2-Butoxy-8-methoxy-9H-purin-6-amine, TFA salt

The product from step (iv) (24 g) was dissolved in absolute methanol (300 ml) and 30 ml of trifluoroacetic acid was added. The reaction mixture was stirred at ambient temperature for 3 days and concentrated in vacuo. The subtitle compound was obtained as a white crystalline solid after trituration with methanol/ethyl acetate. Yield 21 g.

$^1$H NMR δ (CD$_3$OD) 4.48 (2H, t), 4.15 (3H, s), 1.80 (2H, quintet), 1.50 (2H, sextet), 0.99 (3H, t).

(vi) 9-(3-Bromopropyl)-2-butoxy-8-methoxy-9H-purin-6-amine

The product of step (v) (20 g) was added in portions over 10 minutes to a rapidly stirred mixture of potassium carbonate (40 g) and 1,3-dibromopropane (34 ml) in N,N-dimethylformamide (250 ml) at ambient temperature and the mixture stirred for 1.5 hours. The mixture was diluted with water and extracted with ethyl acetate. The combined extracts were washed with brine and dried. The mixture was purified by column chromatography (ethyl acetate), to afford the subtitle compound as a white solid. Yield 16 g.

$^1$H NMR δ (CDCl$_3$) 5.19 (2H, s), 4.28 (2H, J=6.7 Hz, t), 4.12 (3H, s), 4.09 (2H, J=9.4 Hz, t), 3.37 (2H, J=13.3 Hz, t), 2.39-2.30 (2H, m), 1.81-1.72 (2H, m), 1.55-1.43 (2H, m), 0.96 (3H, J=11.4 Hz, t).

(vii) 6-Amino-9-(3-bromopropyl)-2-butoxy-7,9-dihydro-8H-purin-8-one

The product of step (vi) (35.8 g) was dissolved in methanol (400 ml) and treated with 4M hydrogen chloride in dioxane (100 ml). The mixture was stirred at ambient temperature for 6 hours and concentrated in vacuo. Dichloromethane (500 ml) was added and concentrated in vacuo, which afforded a foam that was taken onto the next step without further purification. Yield 38 g.

$^1$H NMR δ (DMSO-d$_6$) 10.60 (1H, s), 4.45 (2H, m), 3.84 (2H, m), 3.65 (2H, m), 2.19 (2H, m), 1.66-1.73 (2H, m), 1.36-1.47 (2H, m), 0.96 (3H, m).

(viii) 6-Amino-2-butoxy-9-{3-[(3-morpholin-4-ylpropyl)amino]propyl}-7,9-dihydro-8H-purin-8-one The product of step (vii) (4 g) was suspended in acetonitrile (40 ml) and 4-(3-aminopropyl)morpholine (15 ml) was added. The mixture was stirred under reflux for 14 h. then the mixture evaporated under reduced pressure. The residue was purified by RPHPLC. Yield 3.59 g.

MS: APCI (+ve): 408 (M+H)

(ix) 6-Amino-9-{3-[benzyl(3-morpholin-4-ylpropyl)amino]propyl}-2-butoxy-7,9-dihydro-8H-purin-8-one 6-Amino-2-butoxy-9-[3-(3-morpholin-4-yl-propylamino)-propyl]-7,9-dihydro-purin-8-one (0.1 g), Benzaldehyde (0.03125 g, 0.03005 ml) were combined in NMP (1.5 mL) and stirred at RT for 15 mins. Sodium triacetoxyborohydride (0.078 g) was added and the reaction mixture was stirred for 16 h. The reaction mixture was diluted with methanol and purified by RPHPLC to give the title compound (0.068 g)

$^1$H NMR δ (DMSO-d$_6$) 0.90 (3H, t), 1.31-1.42 (2H, m), 1.44-1.54 (2H, m), 1.56-1.67 (2H, m), 1.77-1.88 (2H, m), 2.14-2.30 (6H, m), 2.32-2.44 (4H, m), 3.43-3.52 (6H, m), 3.64-3.72 (2H, m), 4.06-4.17 (2H, m), 6.37 (2H, s), 7.17-7.29 (5H, m), 9.80 (1H, s)

MS: APCI (+ve): 498 (M+H)

Examples 2-16 were prepared by the method of example 1

Example 2

6-Amino-2-butoxy-9-{3-[(4-isopropoxybenzyl)(3-morpholin-4-ylpropyl)amino]propyl}-7,9-dihydro-8H-purin-8-one

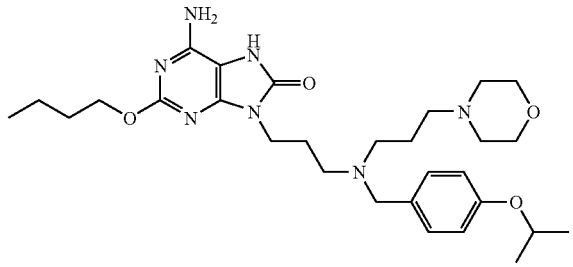

¹H NMR δ (DMSO-d₆) 0.82-0.95 (3H, m), 1.30-1.40 (4H, m), 1.43-1.53 (2H, m), 1.57-1.67 (2H, m), 1.76-1.86 (2H, m), 2.15-2.24 (3H, m), 2.30-2.39 (3H, m), 2.67 (1H, s), 2.99-3.09 (4H, m), 3.39 (2H, s), 3.44-3.54 (4H, m), 3.61-3.77 (6H, m), 4.12 (2H, t), 6.38 (2H, s), 6.82 (2H, d), 7.10 (2H, d)

MS: APCI (+ve): 556 (M+H)

Example 3

6-Amino-2-butoxy-9-{3-[(4-methoxybenzyl)(3-morpholin-4-ylpropyl)amino]propyl}-7,9-dihydro-8H-purin-8-one

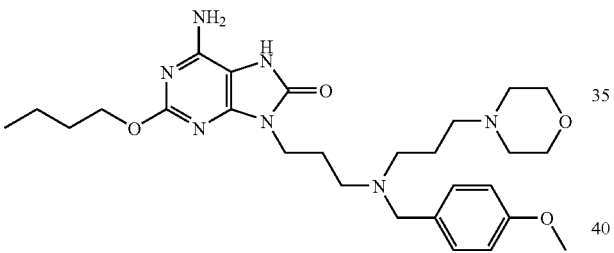

¹H NMR δ (DMSO-d₆) 0.90 (3H, t), 1.32-1.42 (2H, m), 1.44-1.53 (2H, m), 1.57-1.66 (2H, m), 1.77-1.86 (2H, m), 2.14-2.26 (6H, m), 2.29-2.42 (4H, m), 3.42 (2H, s), 3.45-3.52 (4H, m), 3.63-3.71 (2H, m), 3.72 (3H, s), 4.08-4.16 (2H, m), 6.38 (2H, s), 6.82 (2H, d), 7.16 (2H, d), 9.82 (1H, s)

MS: APCI (+ve): 528 (M+H)

Example 4

6-Amino-2-butoxy-9-{3-[(2,3-dihydro-1,4-benzodioxin-6-ylmethyl)(3-morpholin-4-ylpropyl)amino]propyl}-7,9-dihydro-8H-purin-8-one

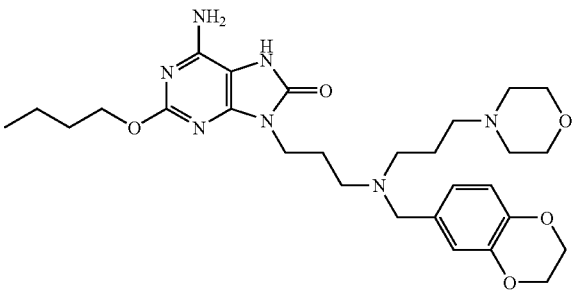

¹H NMR δ (DMSO-d₆) 0.90 (3H, t), 1.31-1.41 (2H, m), 1.43-1.52 (2H, m), 1.57-1.66 (2H, m), 1.75-1.85 (2H, m), 2.15-2.26 (6H, m), 2.29-2.41 (6H, m), 3.45-3.53 (4H, m), 3.63-3.71 (2H, m), 4.12 (2H, t), 4.20 (4H, s), 6.37 (2H, s), 6.66-6.77 (3H, m), 9.81 (1H, s)

MS: APCI (+ve): 556 (M+H)

Example 5

6-Amino-2-butoxy-9-{3-[(3,4-dimethoxybenzyl)(3-morpholin-4-ylpropyl)amino]propyl}-7,9-dihydro-8H-purin-8-one

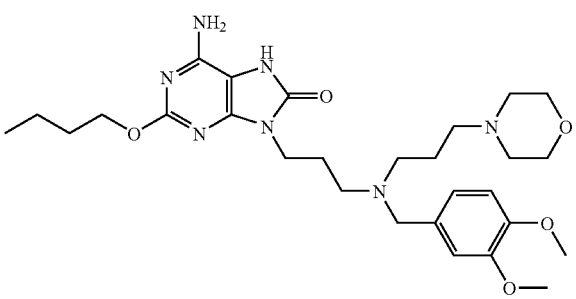

¹H NMR δ (DMSO-d₆) 0.90 (3H, t), 1.31-1.42 (2H, m), 1.43-1.54 (2H, m), 1.55-1.65 (2H, m), 1.77-1.87 (2H, m), 2.12-2.26 (6H, m), 2.30-2.44 (4H, m), 3.30 (1H, s), 3.40-3.52 (6H, m), 3.65-3.76 (7H, m), 4.12 (2H, t), 6.37 (2H, s), 6.73-6.77 (1H, m), 6.82 (1H, d), 6.89 (1H, d), 9.81 (1H, s)

MS: APCI (+ve): 558 (M+H)

Example 6

6-Amino-2-butoxy-9-{3-[(4-morpholin-4-ylbenzyl)(3-morpholin-4-ylpropyl)amino]propyl}-7,9-dihydro-8H-purin-8-one

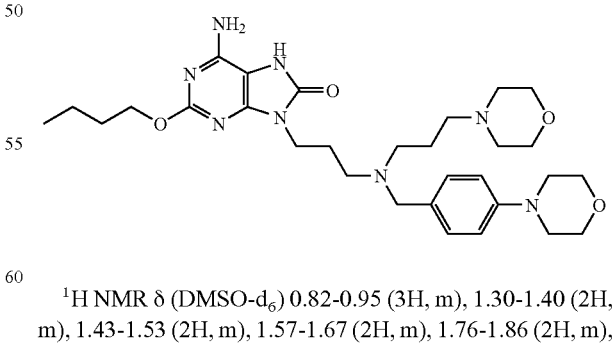

¹H NMR δ (DMSO-d₆) 0.82-0.95 (3H, m), 1.30-1.40 (2H, m), 1.43-1.53 (2H, m), 1.57-1.67 (2H, m), 1.76-1.86 (2H, m), 2.15-2.24 (6H, m), 2.30-2.39 (4H, m), 2.99-3.09 (4H, m), 3.39 (2H, s), 3.44-3.54 (4H, m), 3.61-3.77 (6H, m), 4.12 (2H, t), 6.38 (2H, s), 6.82 (2H, d), 7.10 (2H, d)

MS: APCI (+ve): 583 (M+H)

Example 7

6-Amino-2-butoxy-9-{3-[(3-morpholin-4-ylpropyl)(4-pyrimidin-2-ylbenzyl)amino]propyl}-7,9-dihydro-8H-purin-8-one

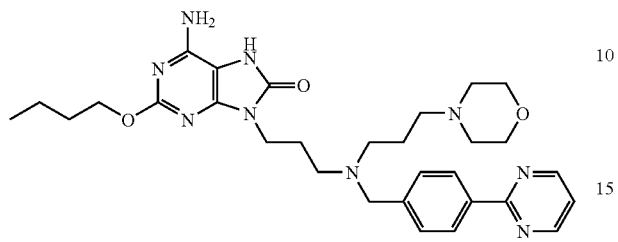

$^1$H NMR δ (DMSO-$d_6$) 0.87 (3H, t), 1.28-1.39 (2H, m), 1.47-1.55 (2H, m), 1.56-1.64 (2H, m), 1.82-1.90 (2H, m), 2.13-2.26 (6H, m), 2.31-2.43 (4H, m), 3.46 (4H, t), 3.58 (2H, s), 3.67-3.75 (2H, m), 4.11 (2H, t), 6.36 (2H, s), 7.40-7.48 (3H, m), 8.32 (2H, d), 8.89 (2H, d), 9.81 (1H, s)

MS: APCI (+ve): 576 (M+H)

Example 8

6-Amino-2-butoxy-9-{3-[[4-(methylthio)benzyl](3-morpholin-4-ylpropyl)amino]propyl}-7,9-dihydro-8H-purin-8-one

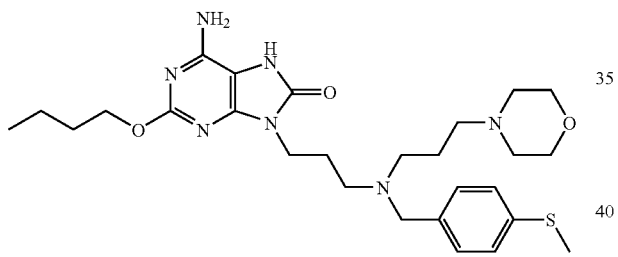

$^1$H NMR δ (DMSO-$d_6$) 0.90 (3H, t), 1.29-1.41 (2H, m), 1.43-1.52 (2H, m), 1.56-1.66 (2H, m), 1.78-1.87 (2H, m), 2.14-2.24 (6H, m), 2.31-2.41 (4H, m), 2.44 (3H, s), 3.41-3.51 (6H, m), 3.69 (2H, t), 4.12 (2H, t), 6.38 (2H, s), 7.19 (4H, dd), 9.81 (1H, s)

MS: APCI (+ve): 544 (M+H)

Example 9

6-Amino-2-butoxy-9-(3-{(3-morpholin-4-ylpropyl)[(2-oxo-2H-chromen-6-yl)methyl]amino}propyl)-7,9-dihydro-8H-purin-8-one

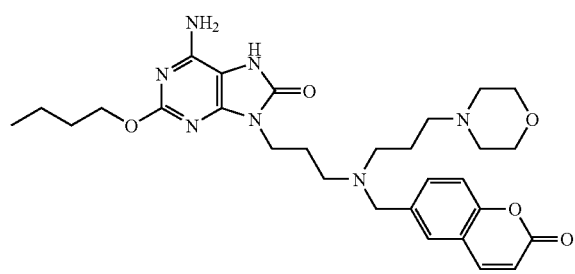

$^1$H NMR δ (DMSO-$d_6$) 0.88 (3H, t), 1.28-1.39 (2H, m), 1.45-1.54 (2H, m), 1.55-1.64 (2H, m), 1.79-1.88 (2H, m), 2.14-2.26 (6H, m), 2.34-2.46 (4H, m), 3.45 (4H, t), 3.55 (2H, s), 3.70 (2H, t), 4.10 (2H, t), 6.37 (2H, s), 6.47 (1H, d), 7.31 (1H, d), 7.54 (1H, dd), 7.61 (1H, d), 8.03 (1H, d), 9.80 (1H, s)

MS: APCI (+ve): 566 (M+H)

Example 10

6-Amino-2-butoxy-9-(3-{(3-morpholin-4-ylpropyl)[(2-oxo-2,3-dihydro-1,3-benzothiazol-6-yl)methyl]amino}propyl)-7,9-dihydro-8H-purin-8-one

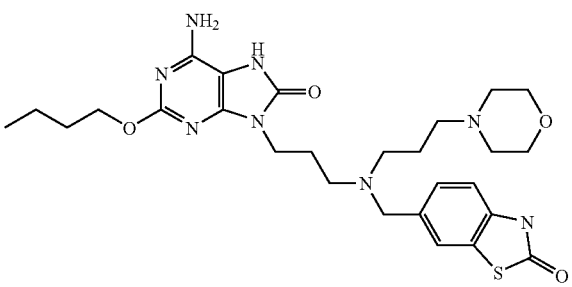

$^1$H NMR δ (DMSO-$d_6$) 0.89 (3H, t), 1.26-1.41 (2H, m), 1.42-1.51 (2H, m), 1.55-1.64 (2H, m), 1.76-1.89 (2H, m), 2.11-2.24 (6H, m), 2.27-2.44 (4H, m), 3.40-3.53 (6H, m), 3.62-3.76 (2H, m), 4.11 (2H, t), 6.37 (2H, s), 7.02 (1H, d), 7.18 (1H, d), 7.45 (1H, s), 9.69-9.90 (1H, m)

MS: APCI (+ve): 571 (M+H)

Example 11

6-Amino-2-butoxy-9-{3-[(3-morpholin-4-ylpropyl)(4-propoxybenzyl)amino]propyl}-7,9-dihydro-8H-purin-8-one

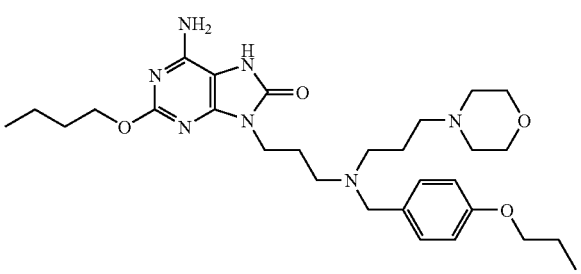

$^1$H NMR δ (DMSO-$d_6$) 0.83-1.02 (6H, m), 1.29-1.43 (2H, m), 1.42-1.56 (2H, m), 1.54-1.87 (6H, m), 2.12-2.26 (6H, m), 2.28-2.42 (4H, m), 3.41 (2H, s), 3.43-3.53 (4H, m), 3.62-3.72 (2H, m), 3.88 (2H, t), 4.12 (2H, t), 6.37 (2H, s), 6.81 (2H, d), 7.15 (2H, d), 9.81 (1H, s)

MS: APCI (+ve): 556 (M+H)

Example 12

6-Amino-2-butoxy-9-{3-[(3,5-dimethoxybenzyl)(3-morpholin-4-ylpropyl)amino]propyl}-7,9-dihydro-8H-purin-8-one

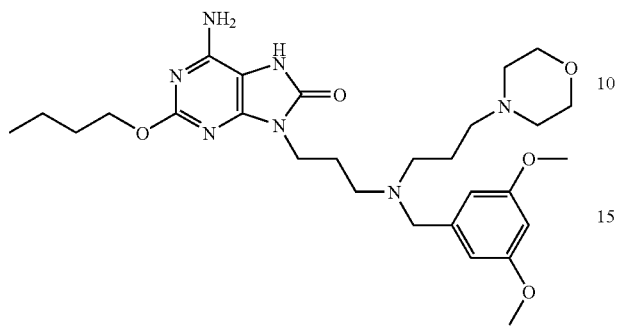

¹H NMR δ (DMSO-d₆) 0.90 (3H, t), 1.32-1.40 (2H, m), 1.45-1.53 (2H, m), 1.56-1.65 (2H, m), 1.77-1.85 (2H, m), 2.17-2.25 (6H, m), 2.31-2.43 (4H, m), 3.44 (2H, s), 3.48 (4H, t), 3.64-3.70 (2H, m), 3.71 (6H, s), 4.11 (2H, t), 6.33 (1H, t), 6.38 (2H, s), 6.47 (2H, d)

MS: APCI (+ve): 558 (M+H)

Example 13

6-Amino-2-butoxy-9-{3-[(2,4-dimethoxybenzyl)(3-morpholin-4-ylpropyl)amino]propyl}-7,9-dihydro-8H-purin-8-one

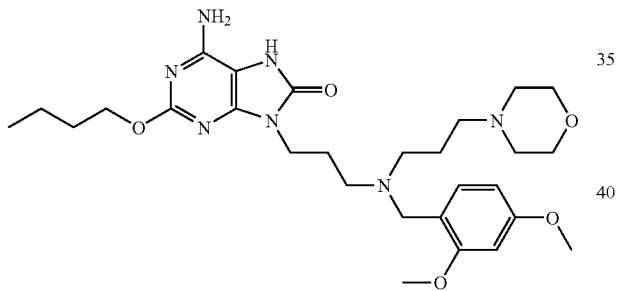

¹H NMR δ (DMSO-d₆) 0.90 (3H, t), 1.30-1.41 (2H, m), 1.42-1.53 (2H, m), 1.56-1.67 (2H, m), 1.75-1.86 (2H, m), 2.14-2.25 (6H, m), 2.30-2.41 (4H, m), 3.40 (2H, s), 3.45-3.53 (4H, m), 3.66 (2H, t), 3.73 (6H, s), 4.12 (2H, t), 6.37 (2H, s), 6.39-6.44 (1H, m), 6.48 (1H, d), 7.14 (1H, d), 9.80 (1H, s)

MS: APCI (+ve): 558 (M+H)

Example 14

(4-{[[3-(6-Amino-2-butoxy-8-oxo-7,8-dihydro-9H-purin-9-yl)propyl](3-morpholin-4-ylpropyl)amino]methyl}phenoxy)acetonitrile

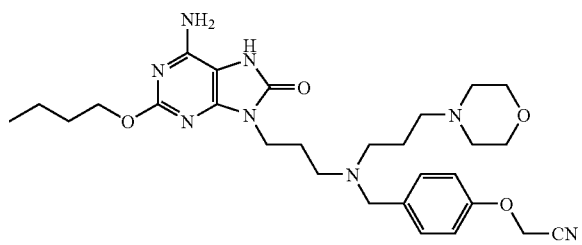

¹H NMR δ (DMSO-d₆) 0.90 (3H, t), 1.30-1.42 (2H, m), 1.43-1.53 (2H, m), 1.56-1.66 (2H, m), 1.77-1.86 (2H, m), 2.12-2.25 (6H, m), 2.30-2.43 (4H, m), 3.42-3.51 (6H, m), 3.68 (2H, t), 4.12 (2H, t), 5.13 (2H, s), 6.38 (2H, s), 6.96 (2H, d), 7.26 (2H, d), 9.81 (1H, s)

MS: APCI (+ve): 553 (M+H)

Example 15

6-Amino-2-butoxy-9-{3-[(3-morpholin-4-ylpropyl)(4-pyrrolidin-1-ylbenzyl)amino]propyl}-7,9-dihydro-8H-purin-8-one

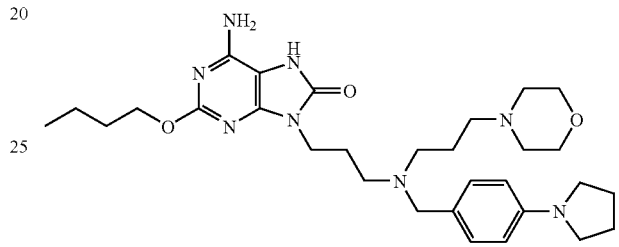

¹H NMR δ (DMSO-d₆) 0.90 (3H, t), 1.32-1.41 (2H, m), 1.44-1.53 (2H, m), 1.58-1.67 (2H, m), 1.78-1.84 (2H, m), 1.90-1.96 (4H, m), 2.15-2.26 (6H, m), 2.31-2.37 (4H, m), 3.15-3.21 (4H, m), 3.36 (2H, s), 3.49 (4H, t), 3.67 (2H, t), 4.13 (2H, t), 6.37 (2H, s), 6.42 (2H, d), 7.02 (2H, d), 9.80 (1H, s)

MS: APCI (+ve): 567 (M+H)

Example 16

6-Amino-2-butoxy-9-(3-{(3-morpholin-4-ylpropyl)[4-(1H-1,2,4-triazol-1-yl)benzyl]amino}propyl)-7,9-dihydro-8H-purin-8-one

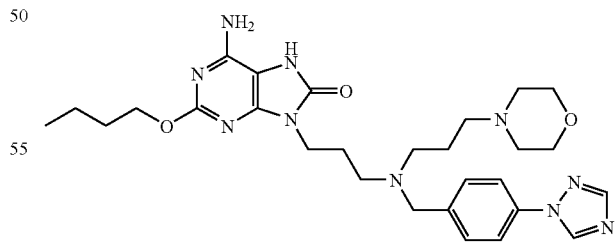

¹H NMR δ (DMSO-d₆) 0.87 (3H, t), 1.28-1.39 (2H, m), 1.46-1.55 (2H, m), 1.55-1.65 (2H, m), 1.80-1.90 (2H, m), 2.15-2.26 (6H, m), 2.29-2.46 (4H, m), 3.41-3.51 (4H, m), 3.56 (2H, s), 3.71 (2H, t), 4.10 (2H, t), 6.37 (2H, s), 7.47 (2H, d), 7.76 (2H, d), 8.19 (2H, d), 9.84 (1H, s)

MS: APCI (+ve): 565 (M+H)

Example 17

6-Amino-2-butoxy-9-{3-[[4-(methylsulfonyl)benzyl](3-morpholin-4-ylpropyl)amino]propyl}-7,9-dihydro-8H-purin-8-one

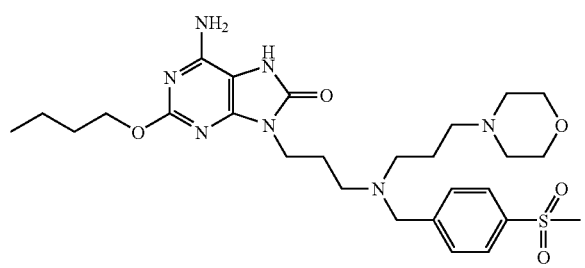

The product from example 1 step (viii) (0.1 g), 4-methylsulphonylbenzyl bromide (0.0673 g) and potassium carbonate (0.0373 g) were combined in DMF (1.5 mL) and stirred at RT for 15 hrs. The reaction mixture was diluted with methanol filtered and purified by RPHPLC to give title compound, 0.039 g $^1$H NMR δ (DMSO-$d_6$) 0.82-0.98 (3H, m), 1.27-1.43 (2H, m), 1.43-1.55 (2H, m), 1.56-1.68 (2H, m), 1.79-1.91 (2H, m), 2.13-2.30 (6H, m), 2.33-2.42 (4H, m), 3.18 (4H, s), 3.41-3.54 (2H, m), 3.61 (2H, s), 3.66-3.79 (2H, m), 4.12 (2H, t), 6.38 (2H, s), 7.57 (2H, d), 7.83 (2H, d), 8.14 (1H, s), 9.82 (1H, s)

MS: APCI (+ve): 576 (M+H)

Example 18

4-{[[3-(6-Amino-2-butoxy-8-oxo-7,8-dihydro-9H-purin-9-yl)propyl](3-morpholin-4-ylpropyl)amino]methyl}-N-(tert-butyl)benzenesulfonamide

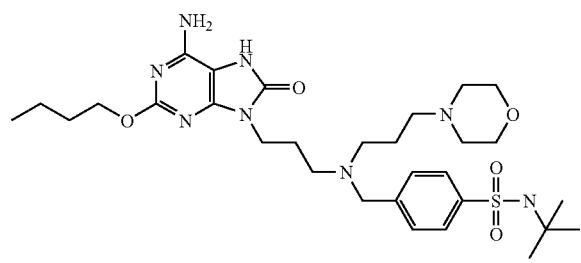

The title compound was prepared using the method of example 17

$^1$H NMR δ (DMSO-$d_6$) 0.89 (3H, t), 1.06 (9H, s), 1.32-1.43 (2H, m), 1.40-1.51 (2H, m), 1.54-1.69 (2H, m), 1.76-1.91 (2H, m), 2.11-2.24 (6H, m), 2.25-2.40 (4H, m), 3.42-3.50 (4H, m), 3.57 (2H, s), 3.64-3.78 (2H, m), 4.12 (2H, t), 6.38 (2H, s), 7.39-7.53 (3H, m), 7.74 (2H, d), 8.15 (1H, s)

MS: APCI (+ve): 633 (M+H)

Example 19

6-Amino-2-butoxy-9-{3-[[4-(hydroxymethyl)benzyl](3-morpholin-4-ylpropyl)amino]propyl}-7,9-dihydro-8H-purin-8-one

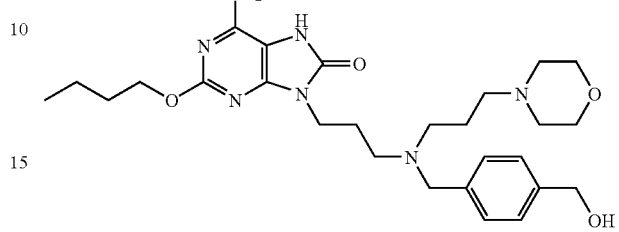

$^1$H NMR δ (DMSO-$d_6$) 0.90 (3H, t), 1.31-1.42 (2H, m), 1.44-1.54 (2H, m), 1.56-1.67 (2H, m), 1.77-1.87 (2H, m), 2.15-2.25 (6H, m), 2.30-2.42 (4H, m), 3.45-3.50 (5H, m), 3.67 (2H, t), 4.13 (2H, t), 4.46 (2H, d), 5.09 (1H, t), 6.37 (2H, s), 7.21 (4H, s), 9.81 (1H, s)

MS: APCI (+ve): 528 (M+H)

Example 20

6-Amino-9-(3-{benzyl[2-(dimethylamino)ethyl]amino}propyl)-2-butoxy-7,9-dihydro-8H-purin-8-one

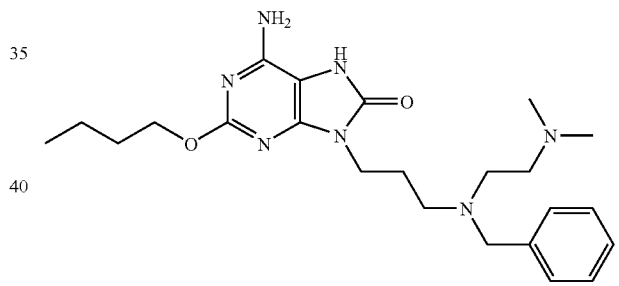

(i) 9-(3-Chloropropyl)-2-butoxy-8-methoxy-9H-purin-6-amine

The product of example 1 step (v) (50 g) was added in portions over 10 minutes to a rapidly stirred mixture of potassium carbonate (60 g) and 1-bromo-3-chloropropane (21 ml) in dimethylformamide (400 ml) at ambient temperature and the mixture stirred for 3 hours. The mixture was diluted with water and extracted with ethyl acetate. The combined extracts were washed with water and dried. The crude product was recrystallised from acetonitrile. Yield 29.83 g.

MS: ESI (+ve): 314

(ii) 6-Amino-9-(3-chloropropyl)-2-butoxy-7,9-dihydro-8H-purin-8-one

The product of step (i) (29.8 g) was dissolved in methanol (60 ml) and treated with 4M hydrogen chloride in dioxane (60 ml). The mixture was stirred at room temperature for 2 hours, cooled to 0° C. and neutralised with 3.5% aqueous ammonia solution. The solid was filtered off, washed with water then methanol and dried Yield 27.2 g.

¹H NMR δ (DMSO-d₆) 9.88 (1H, s), 6.41 (2H, s), 4.15 (2H, t), 3.80 (2H, t), 3.65 (2H, t), 2.14-2.07 (2H, m), 1.68-1.61 (2H, m), 1.43-1.34 (2H, m), 0.92 (3H, t).

(iii) 6-Amino-2-butoxy-9-(3-{[2-(dimethylamino) ethyl]amino}propyl)-7,9-dihydro-8H-purin-8-one, hydrochloride The product of step (ii) (16 g), DMSO (16 ml) and N,N-dimethylethylenediamine (120 ml) was heated at 80° C. for 4 h then evaporated under reduced pressure. The residue was azeotroped with acetonitrile then heated under reflux in acetonitrile (250 ml) for 30 min then cooled to 0° C. for 1 h. The solid was filtered off and dried. Yield 15.32 g.

¹H NMR δ (DMSO-d₆) 10.60 (1H, brs), 6.68 (2H, s), 4.15 (2H, t), 3.74 (2H, t), 2.96 (2H, t), 2.97 (2H, t), 2.54-2.51 (2H, m), 2.22 (6H, s), 2.02-1.95 (2H, m), 1.68-1.61 (2H, m), 1.44-1.35 (2H, m), 0.92 (3H, t).

MS: ESI (+ve): 352

(iv) 6-Amino-9-(3-{benzyl[2-(dimethylamino)ethyl] amino}propyl)-2-butoxy-7,9-dihydro-8H-purin-8-one The product from step (iii) (0.1 g) and benzaldehyde (0.0362 g, 0.0347 ml) were combined in NMP (4 mL) and stirred at RT for 15 mins. Sodium triacetoxyborohydride (0.0904 g) was added. The reaction mixture was stirred for 16 h. The reaction mixture was diluted with methanol and purified by RP-prep-HPLC 75:05 NH3:acetonitrile over 15 mins to give title compound (0.068 g)

¹H NMR δ (DMSO-d₆) 0.90 (3H, t), 1.31-1.42 (2H, m), 1.54-1.65 (2H, m), 1.77-1.88 (2H, m), 2.04 (6H, s), 2.21-2.28 (2H, m), 2.39-2.47 (4H, m), 3.53 (2H, s), 3.64-3.72 (2H, m), 4.12 (2H, t), 6.40 (2H, s), 7.15-7.25 (1H, m), 7.28 (4H, s)

MS: APCI (+ve): 442 (M+H)

Example 21

6-Amino-9-{3-[benzyl(1-methylpiperidin-4-yl) amino]propyl}-2-butoxy-7,9-dihydro-8H-purin-8-one

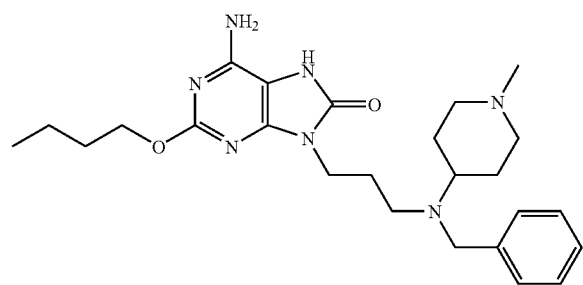

The title compound was prepared by the method of example 1 using 1-methylpiperidin-4-amine.

¹H NMR δ (DMSO-d₆) 0.83-0.98 (3H, m), 1.30-1.54 (4H, m), 1.54-1.67 (3H, m), 1.67-1.80 (3H, m), 2.09 (4H, s), 2.31-2.47 (4H, m), 2.70-2.80 (2H, m), 3.55 (2H, s), 3.59-3.69 (2H, m), 4.12 (2H, t), 6.36 (2H, s), 7.12-7.33 (5H, m), 9.78 (1H, s)

MS: APCI (+ve): 468 (M+H)

The invention claimed is:

1. A compound of formula (I):

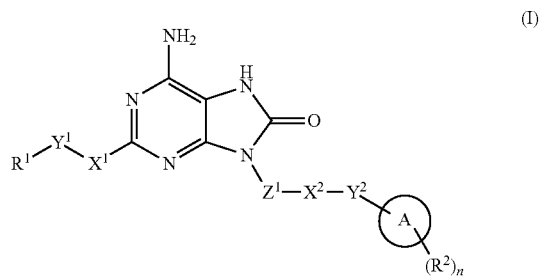

wherein $R^1$ represents hydrogen, hydroxyl, $C_1$-$C_6$ alkoxy, $C_2$-$C_5$ alkoxycarbonyl, $C_1$-$C_6$ haloalkyl, $C_1$-$C_6$ haloalkoxy, or a $C_6$-$C_{10}$ aryl, $C_5$-$C_{10}$ heteroaryl or $C_3$-$C_8$ cycloalkyl group, each group being optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, $C_2$-$C_5$ alkoxycarbonyl, amino (NH₂) and di-$C_1$-$C_6$ alkylamino;

$Y^1$ represents a single bond or $C_1$-$C_6$ alkylene;

$X^1$ represents a single bond or an oxygen or sulphur atom or sulphonyl (SO₂) or $NR^3$;

$Z^1$ represents a $C_2$-$C_6$ alkylene or $C_3$-$C_s$ cycloalkylene group, each of which may be optionally substituted by at least one hydroxyl;

$X^2$ represents $NR^4$, $CONR^4$, $NR^4CO$, $SO_2NR^4$, $NR^4CONR^5$, $NR^5CONR^4$, $SO_2$, $CO$ or $NR^5CSNR^5$;

$Y^2$ represents a single bond or $C_1$-$C_6$ alkylene;

n is 0, 1 or 2;

each $R^2$ group independently represents halogen, cyano, $S(O)_mR^9$, $OR^{10}$, $SO_2NR^{10}R^{11}$, $CONR^{10}R^{11}$, $NR^7R^8$, $NR^{10}SO_2R^9$, $NR^{10}CO_2R^9$, $NR^{10}COR^9$, $C_6$-$C_{10}$ aryl, $C_5$-$C_{10}$ heteroaryl, $C_1$-$C_6$ alkyl, $C_2$-$C_6$ alkenyl, $C_2$-$C_6$ alkynyl or $C_3$-$C_8$ cycloalkyl group, the latter six groups being optionally substituted by one or more substituents independently selected from halogen, cyano, $S(O)_mR^{12}$, $OR^{13}$, $SO_2NR^{13}R^{14}$, $CONR^{13}R^{14}$, $NR^7R^8$, $NR^{13}SO_2R^{12}$, $NR^{13}CO_2R^{12}$, $NR^{13}COR^{12}$, $C_1$-$C_6$ alkyl or $C_3$-$C_8$ cycloalkyl;

$R^3$ represents hydrogen or $C_1$-$C_6$ alkyl;

$R^4$ represents hydrogen or a 3- to 8-membered saturated heterocyclic ring comprising a ring group O or $NR^6$, or $R^4$ represents a $C_1$-$C_6$ alkylene optionally substituted by one or more substituents independently selected from $NR^7R^8$ or $R^6$;

$R^5$ represents hydrogen or a $C_1$-$C_6$ alkyl or $C_3$-$C_6$ cycloalkyl group, each of which may be optionally substituted by one or more substituents independently selected from halogen, hydroxyl and $NR^7R^8$;

$R^6$ represents hydrogen, $CO_2R^9$, $SO_2R^9$, $COR^9$, $SO_2NR^{10}R^{11}$, $CONR^{10}R^{11}$, a 3- to 8-membered saturated heterocyclic ring comprising a ring group $NR^9$, or (i) a $C_6$-$C_{10}$ aryl or $C_5$-$C_{10}$ heteroaryl group, each of which may be optionally substituted by one or more substituents independently selected from halogen, cyano, oxo, carboxyl, $S(O)_mR^{12}$, $OR^{13}$, $SO_2NR^{13}R^{14}$, $CONR^{13}R^{14}$, $NR^{13}R^{14}$, $NR^{13}SO_2R^{12}$, $NR^{13}CO_2R^{12}$, $NR^{13}COR^{12}$, $C_1$-$C_6$ alkyl and $C_1$-$C_3$ haloalkyl, or (ii) a $C_1$-$C_6$ alkyl, $C_2$-$C_6$ alkenyl, $C_2$-$C_6$ alkynyl or $C_3$-$C_8$ cycloalkyl group, each of which may be optionally substituted by one or more substituents independently selected from halogen, cyano, $C_3$-$C_8$ cycloalkyl, $OR^{15}$, $S(O)_pR^{16}$, $CO_2R^{16}$, $NR^{17}R^{18}$, $CONR^{17}R^{18}$, $NR^{17}COR^{16}$, $SO_2NR^{17}R^{18}$, $NR^{17}SO_2R^{16}$ and substituents defined in (i) above;

$R^7$, $R^8$, $R^{13}$, $R^{14}$, $R^{15}$, $R^{19}$, $R^{20}$, $R^{22}$, $R^{23}$, $R^{24}$ and $R^{25}$ each independently represent hydrogen, $C_1$-$C_6$ alkyl or $C_3$-$C_6$ cycloalkyl; or $R^7$ and $R^8$ together with the nitrogen atom to which they are attached form a 3- to 8-membered saturated heterocyclic ring comprising a ring nitrogen atom and optionally one or more further heteroatoms independently selected from nitrogen, oxygen, sulphur and sulphonyl, the heterocyclic ring being optionally substituted by one or more substituents independently selected from halogen, hydroxyl, carboxyl, cyano, $OR^{21}$, $S(O)_qR^{21}$, $NR^{22}R^{23}$, $C_1$-$C_6$ alkyl and $C_3$-$C_8$ cycloalkyl;

$R^9$, $R^{16}$ and $R^{21}$ each independently represent a $C_1$-$C_6$ alkyl or $C_3$-$C_6$ cycloalkyl group, each of which may be optionally substituted by one or more substituents independently selected from halogen, carboxyl, hydroxyl and $NR^{19}R^{20}$;

either $R^{10}$ represents hydrogen or a $C_1$-$C_6$ alkyl, $C_2$-$C_6$ alkenyl, $C_2$-$C_6$ alkynyl or $C_3$-$C_8$ cycloalkyl group, each of which may be optionally substituted by one or more substituents independently selected from halogen, hydroxyl, carboxyl, cyano, $OR^{21}$, $S(O)_qR^{21}$, $NR^{22}R^{23}$ and $C_3$-$C_8$ cycloalkyl, and $R^{11}$ represents hydrogen or a $C_1$-$C_6$ alkyl or $C_3$-$C_6$ cycloalkyl group, each of which may be optionally substituted by one or more substituents independently selected from halogen, hydroxyl and $NR^{24}R^{25}$; or $R^{10}$ and $R^{11}$ together with the nitrogen atom to which they are attached form a 3- to 8-membered saturated heterocyclic ring comprising at least one heteroatom or heterogroup selected from nitrogen, oxygen, sulphur and sulphonyl, the heterocyclic ring being optionally substituted by one or more substituents independently selected from halogen, hydroxyl, carboxyl, cyano, $OR^{21}$, $S(O)_qR^{21}$, $NR^{22}R^{23}$, $C_1$-$C_6$ alkyl and $C_3$-$C_8$ cycloalkyl;

$R^{12}$ represents $C_1$-$C_6$ alkyl or $C_3$-$C_6$ cycloalkyl;

$R^{17}$ and $R^{18}$ are defined as for $R^{10}$ and $R^{11}$ respectively;

m, p and q each independently represent 0, 1 or 2; and

A represents a monocyclic or bicyclic $C_6$-$C_{10}$ aryl or a monocyclic or bicyclic $C_5$-$C_{12}$ heteroaryl group containing 1-3 heteroatoms;

or a pharmaceutically acceptable salt thereof.

2. The compound according to claim 1 wherein $X^1$ represents oxygen, or a pharmaceutically acceptable salt thereof.

3. The compound according to claim 1 wherein $R^1$ represents hydrogen, or a pharmaceutically acceptable salt thereof.

4. The compound according to claim 1 wherein $Y^1$ represents $C_1$-$C_6$ alkylene, or a pharmaceutically acceptable salt thereof.

5. The compound according to claim 1 wherein $Z^1$ is $C_2$-$C_6$ alkylene, or a pharmaceutically acceptable salt thereof.

6. The compound according to claim 1 wherein $X^2$ represents N—$R^4$, or a pharmaceutically acceptable salt thereof.

7. The compound according to claim 1 wherein $Y^2$ represents $C_1$-$C_6$ alkylene, or a pharmaceutically acceptable salt thereof.

8. The compound according to claim 1 wherein A represents phenyl, or a pharmaceutically acceptable salt thereof.

9. The compound according to claim 1 selected from:
6-Amino-9-{3-[benzyl(3-morpholin-4-ylpropyl)amino] propyl}-2-butoxy-7,9-dihydro-8H-purin-8-one;

6-Amino-2-butoxy-9-{3-[(4-isopropoxybenzyl)(3-morpholin-4-ylpropyl)amino]propyl}-7,9-dihydro-8H-purin-8-one;

6-Amino-2-butoxy-9-{3-[(4-methoxybenzyl)(3-morpholin-4-ylpropyl)amino]propyl}-7,9-dihydro-8H-purin-8-one;

6-Amino-2-butoxy-9-{3-[(2,3-dihydro-1,4-benzodioxin-6-ylmethyl)(3-morpholin-4-ylpropyl)amino]propyl}-7,9-dihydro-8H-purin-8-one;

6-Amino-2-butoxy-9-{3-[(3,4-dimethoxybenzyl)(3-morpholin-4-ylpropyl)amino]propyl}-7,9-dihydro-8H-purin-8-one;

6-Amino-2-butoxy-9-{3-[(4-morpholin-4-ylbenzyl)(3-morpholin-4-ylpropyl)amino]propyl}-7,9-dihydro-8H-purin-8-one;

6-Amino-2-butoxy-9-{3-[(3-morpholin-4-ylpropyl)(4-pyrimidin-2-ylbenzyl)amino]propyl}-7,9-dihydro-8H-purin-8-one;

6-Amino-2-butoxy-9-{3-[[4-(methylthio)benzyl](3-morpholin-4-ylpropyl)amino]propyl}-7,9-dihydro-8H-purin-8-one;

6-Amino-2-butoxy-9-(3-{(3-morpholin-4-ylpropyl)[(2-oxo-2H-chromen-6-yl)methyl]amino}propyl)-7,9-dihydro-8H-purin-8-one;

6-Amino-2-butoxy-9-(3-{(3-morpholin-4-ylpropyl)[(2-oxo-2,3-dihydro-1,3-benzothiazol-6-yl)methyl]amino}propyl)-7,9-dihydro-8H-purin-8-one;

6-Amino-2-butoxy-9-{3-[(3-morpholin-4-ylpropyl)(4-propoxybenzyl)amino]propyl}-7,9-dihydro-8H-purin-8-one;

6-Amino-2-butoxy-9-{3-[(3,5-dimethoxybenzyl)(3-morpholin-4-ylpropyl)amino]propyl}-7,9-dihydro-8H-purin-8-one;

6-Amino-2-butoxy-9-{3-[(2,4-dimethoxybenzyl)(3-morpholin-4-ylpropyl)amino]propyl}-7,9-dihydro-8H-purin-8-one;

(4-{[[3-(6-Amino-2-butoxy-8-oxo-7,8-dihydro-9H-purin-9-yl)propyl] (3-morpholin-4-ylpropyl)amino] methyl}phenoxy)acetonitrile;

6-Amino-2-butoxy-9-{3-[(3-morpholin-4-ylpropyl)(4-pyrrolidin-1-ylbenzyl)amino]propyl}-7,9-dihydro-8H-purin-8-one;

6-Amino-2-butoxy-9-(3-[(3-morpholin-4-ylpropyl)[4-(1H-1,2,4-triazol-1-yl)benzyl]amino 1 propyl)-7,9-dihydro-8H-purin-8-one;

6-Amino-2-butoxy-9-{3-[[4-(methylsulfonyl)benzyl] (3-morpholin-4-ylpropyl)amino]propyl}-7,9-dihydro-8H-purin-8-one;

4-{[[3-(6-Amino-2-butoxy-8-oxo-7,8-dihydro-9H-purin-9-yl)propyl] (3-morpholin-4-ylpropyl)amino]methyl}-N-(tert-butyl)benzenesulfonamide;

6-Amino-2-butoxy-9-{3-[[4-(hydroxymethyl)benzyl] (3-morpholin-4-ylpropyl)amino]propyl}-7,9-dihydro-8H-purin-8-one;

6-Amino-9-(3-{benzyl[2-(dimethylamino)ethyl]amino}propyl)-2-butoxy-7,9-dihydro-8H-purin-8-one; and 6-Amino-9-{3-[benzyl(1-methylpiperidin-4-yl)amino] propyl}-2-butoxy-7,9-dihydro-8H-purin-8-one, and pharmaceutically acceptable salts thereof.

10. A pharmaceutical composition comprising a compound of formula (I) or a pharmaceutically acceptable salt thereof as claimed in claim 1 in association with a pharmaceutically acceptable adjuvant, diluent or carrier.

11. A process for the preparation of a pharmaceutical composition as claimed in claim 9 comprising mixing the compound or a pharmaceutically acceptable salt thereof with the pharmaceutically acceptable adjuvant, diluent or carrier.

12. A pharmaceutical product comprising, in combination, two or more active ingredients including a first active ingredient which is a compound of formula (I) as defined in claim 1, and a second active ingredient which is selected from: a phosphodiesterase inhibitor, a β2 adrenoceptor agonist, a modulator of chemokine receptor function, an inhibitor of kinase function, a protease inhibitor, a glucocorticoid, an anticholinergic agent and a non-steroidal glucocorticoid receptor agonist.

\* \* \* \* \*